United States Patent
Mittal et al.

(10) Patent No.: US 9,713,590 B2
(45) Date of Patent: Jul. 25, 2017

(54) METHOD FOR TREATMENT OF PAIN AND INFLAMMATION

(75) Inventors: Ravindra Mittal, Gujarat (IN); Sunilendu Bhushan Roy, Gujarat (IN); Jay Shantilal Kothari, Gujarat (IN); Shafiq Sheikh, Gujarat (IN)

(73) Assignee: CADILA HEALTHCARE LIMITED, Ahmedabad, Gujarat (IN)

(*) Notice: Subject to any disclaimer, the term of this patent is extended or adjusted under 35 U.S.C. 154(b) by 14 days.

(21) Appl. No.: 14/234,847

(22) PCT Filed: Jan. 5, 2012

(86) PCT No.: PCT/IN2012/000016
§ 371 (c)(1),
(2), (4) Date: Mar. 17, 2014

(87) PCT Pub. No.: WO2013/014680
PCT Pub. Date: Jan. 31, 2013

(65) Prior Publication Data
US 2015/0064254 A1    Mar. 5, 2015

(30) Foreign Application Priority Data
Jul. 28, 2011  (IN) .......... 2156/MUM/2011

(51) Int. Cl.
*A61K 9/107* (2006.01)
*A61K 31/196* (2006.01)
*A61K 9/00* (2006.01)

(52) U.S. Cl.
CPC .......... *A61K 9/1075* (2013.01); *A61K 9/0014* (2013.01); *A61K 31/196* (2013.01)

(58) Field of Classification Search
None
See application file for complete search history.

(56) References Cited

U.S. PATENT DOCUMENTS

| | | | |
|---|---|---|---|
| 5,629,021 A | 5/1997 | Wright | |
| 5,894,019 A | 4/1999 | Hesse et al. | |
| 6,004,566 A * | 12/1999 | Friedman | A61K 9/1075 424/400 |
| 2010/0029781 A1 | 2/2010 | Morris | |

FOREIGN PATENT DOCUMENTS

| | | |
|---|---|---|
| EP | 0 506 197 B1 | 6/1998 |
| EP | 0 671 903 B1 | 12/2001 |
| EP | 1 536 836 B1 | 3/2008 |
| WO | 2008/051186 A2 | 5/2008 |
| WO | 2010/116382 A2 | 10/2010 |
| WO | WO 2010116382 A2 * 10/2010 ........... A61K 9/0014 |

OTHER PUBLICATIONS

Barthel et al. "Randomized Trial of Diclofenac Sodium Gel in Knee Osteoarthritis", Seminars in Arthritis and Rheumatism, Elsevier, Amsterdam, NL, vol. 39, No. 3, Dec. 2009, pp. 203-212.*
"Diclofenac review", MedicaLook, accessed online on Aug. 22, 2016 at http://www.medicalook.com/reviews/Diclofenac.html.*
"Voltaren Emulgel®" FAQs accessed online on Aug. 22, 2016 at https://www.voltaren.ca/products/faq.*
International Preliminary Report Patentability dated Jan. 28, 2014 for Application No. PCT/IN2012/000016.
Barthel H R et al: "Randomized Controlled Trial of Diclofenae Sodium Gel in Knee Osteoarthritis", Seminars in Arthritis and Rheumatism, Elsevier , Amsterdam, NL, vol. 39, No. 3, Dec. 1, 2009, pp. 203-212, XP026774029, ISSN: 0049-0172, DOI: 10.1016/J.SEMARTHRIT.2809.09 .002 [retrieved on Nov. 22, 2009] Figure 2; Table 2.

* cited by examiner

*Primary Examiner* — Carlos Azpuru
*Assistant Examiner* — Casey Hagopian
(74) *Attorney, Agent, or Firm* — Ladas & Parry LLP

(57) ABSTRACT

The present invention relates to a method for the treatment of pain and inflammation. In particular, the present invention relates to a method for the treatment of musculo-skeletal and connective tissue pain/inflammations. Further, the invention relates to reducing the incidence and severity of adverse events resulting from administration of diclofenac. The method comprises administration of a topical pharmaceutical composition of diclofenac or its salts.

9 Claims, 8 Drawing Sheets

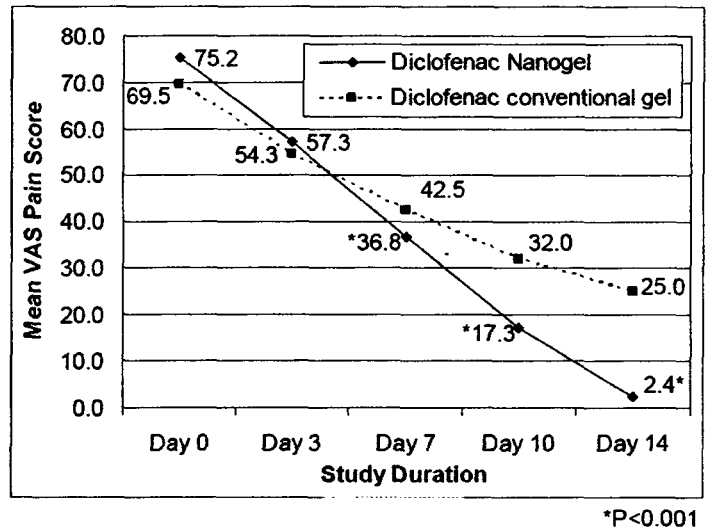
Figure 1: The change in pain intensity score in patients with acute musculoskeletal pain.
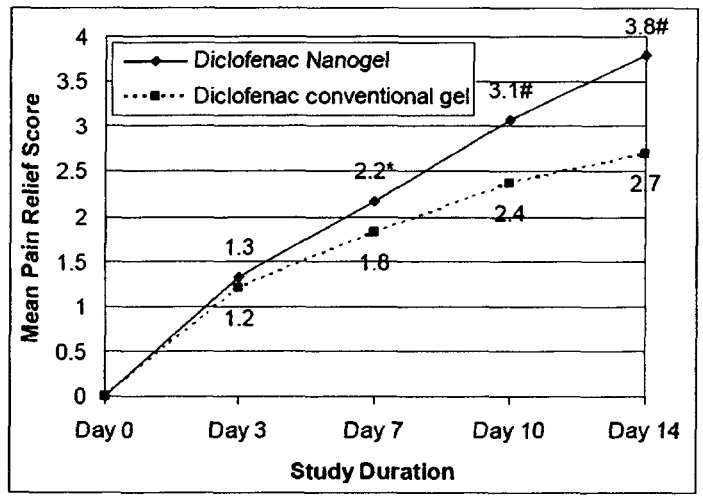
Figure 2: The change in pain relief score in patients with acute musculoskeletal pain.

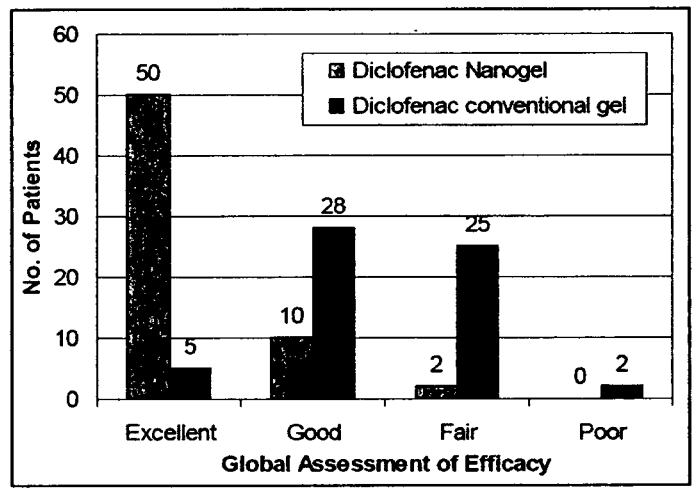
Figure 3: Overall assessment of efficacy at the end of study in patients with acute musculoskeletal pain.
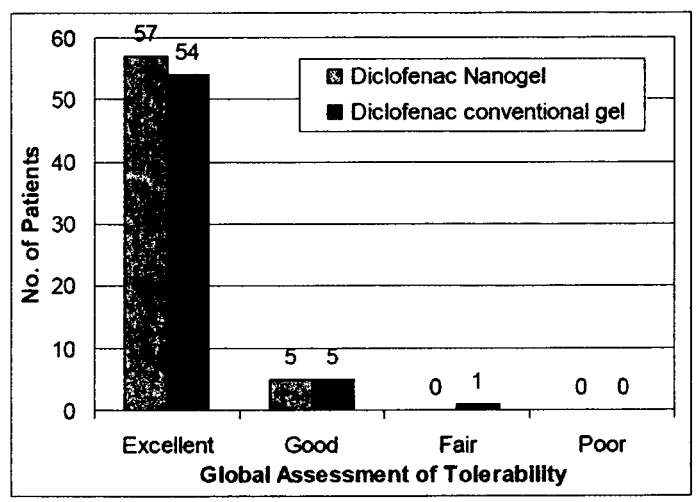
Figure 4: Overall assessment of tolerability at the end of study in patients with acute musculoskeletal pain.

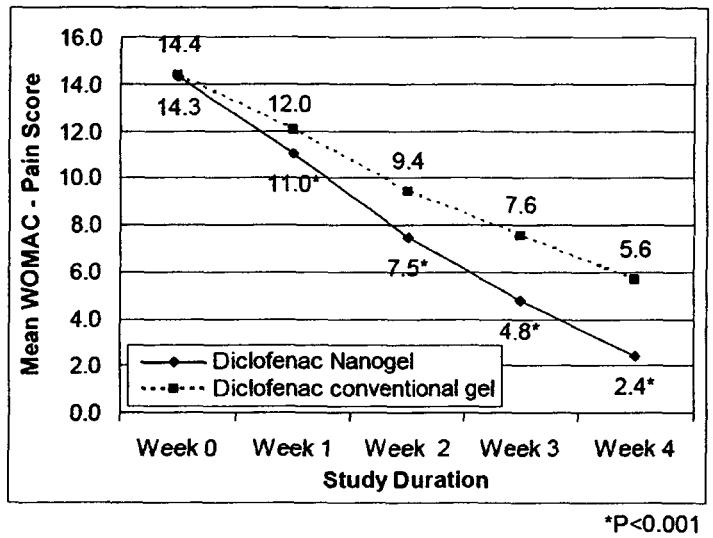
Figure 5: The improvement in WOMAC index pain sub-score in patients with osteoarthritis.
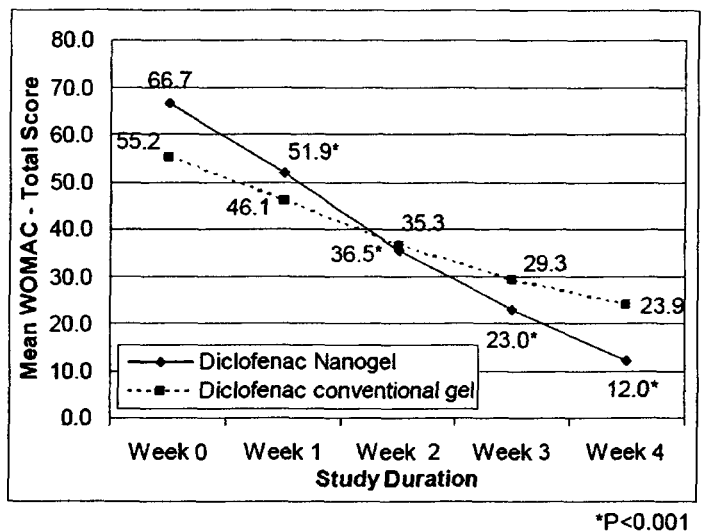
Figure 6: The improvement in WOMAC index total score in patients with osteoarthritis.

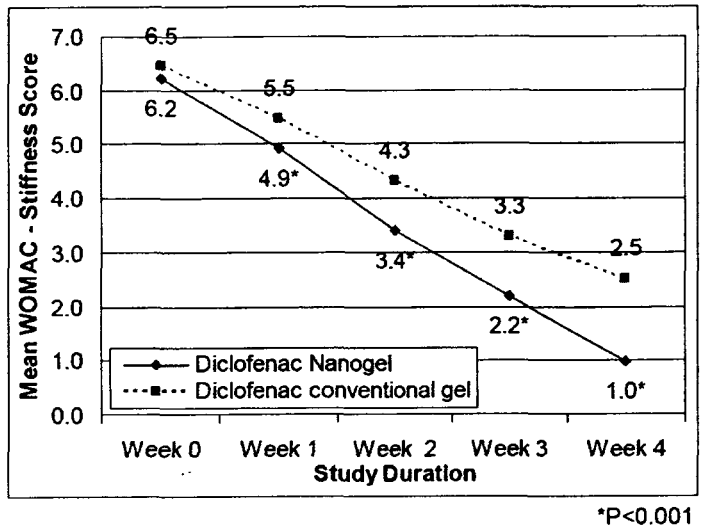
Figure 7: The improvement in WOMAC index stiffness sub-score in patients with osteoarthritis.
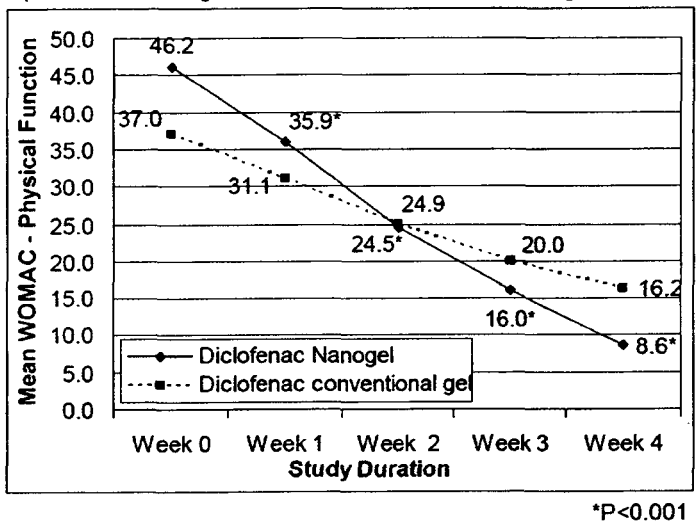
Figure 8: The improvement in WOMAC index physical function sub-score in patients with osteoarthritis.

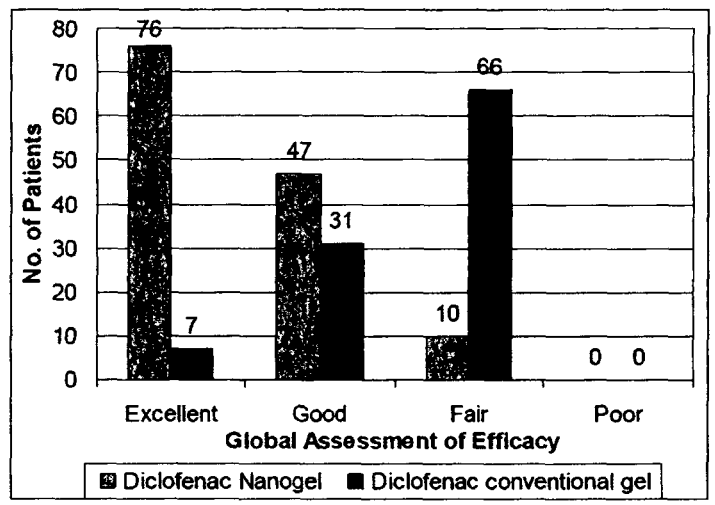
Figure 9: Overall assessment of efficacy at the end of study in patients with osteoarthritis.
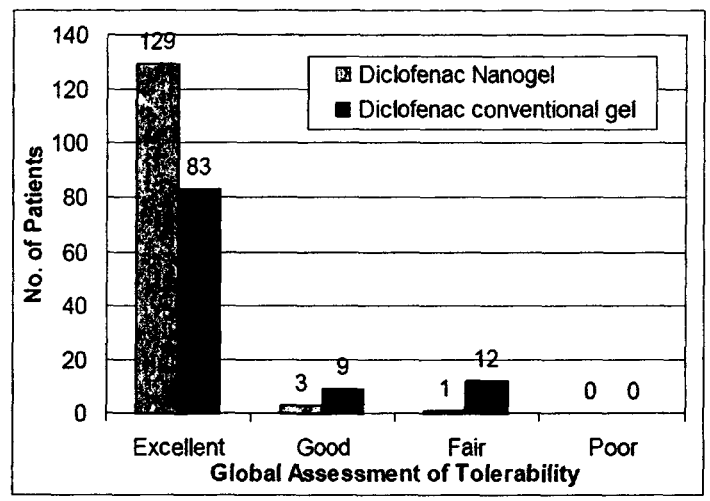
Figure 10: Overall assessment of tolerability at the end of study in patients with osteoarthritis.

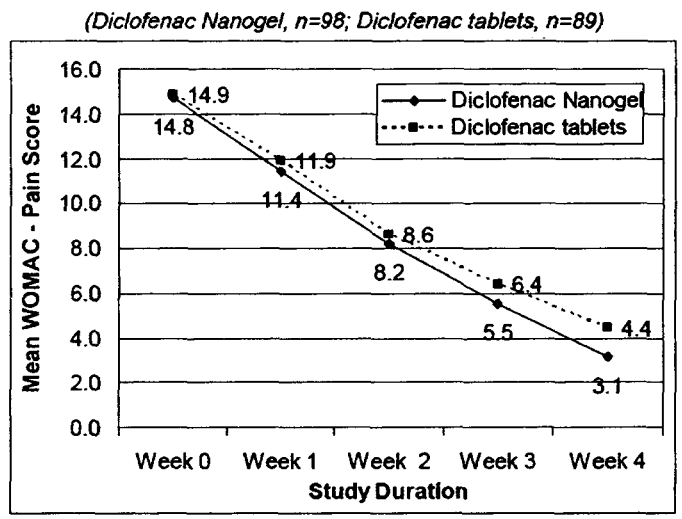
Figure 11: The improvement in WOMAC index pain sub-score in patients with osteoarthritis (Clinical Study B).
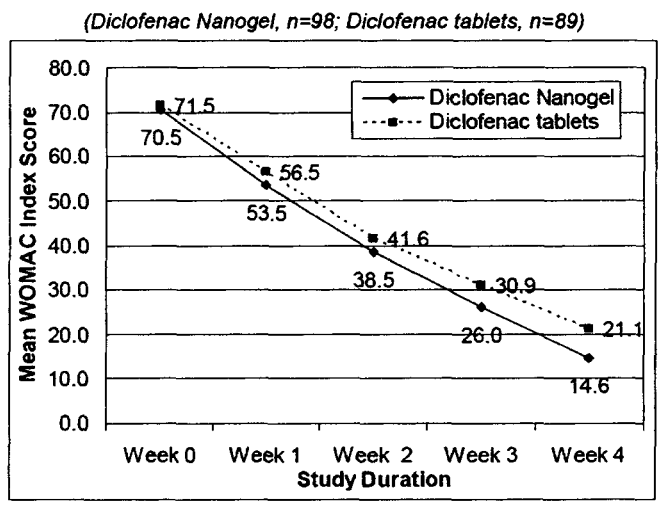
Figure 12: The improvement in WOMAC index total score in patients with osteoarthritis (Clinical Study B).

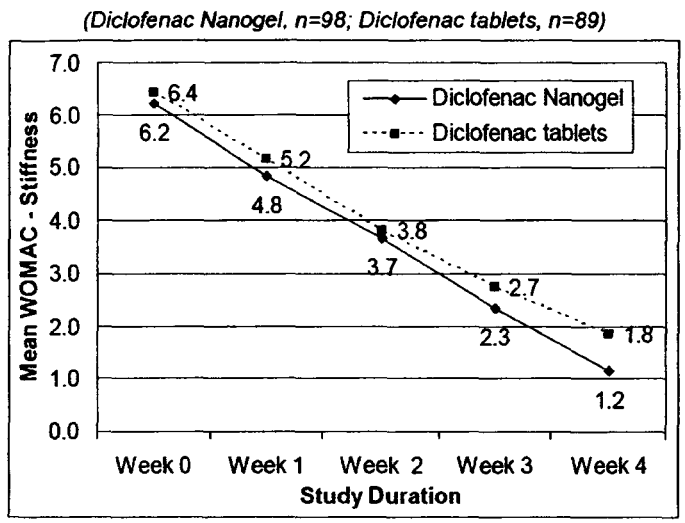
Figure 13: The improvement in WOMAC index stiffness sub-score in patients with osteoarthritis (Clinical Study B).
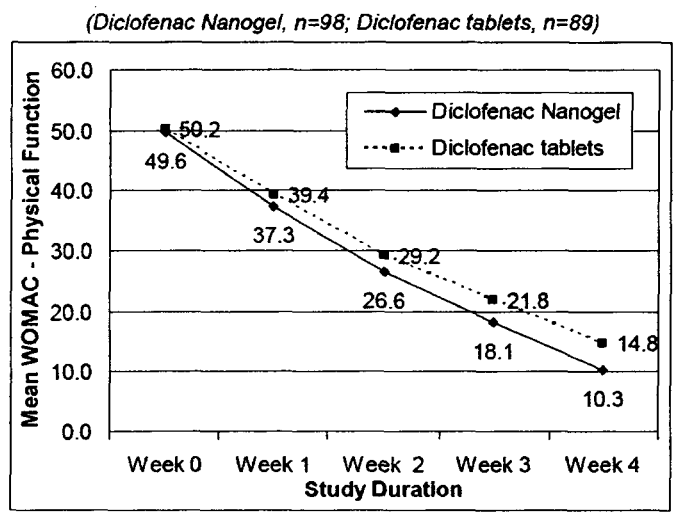
Figure 14: The improvement in WOMAC index physical function sub-score in patients with osteoarthritis (Clinical Study B).

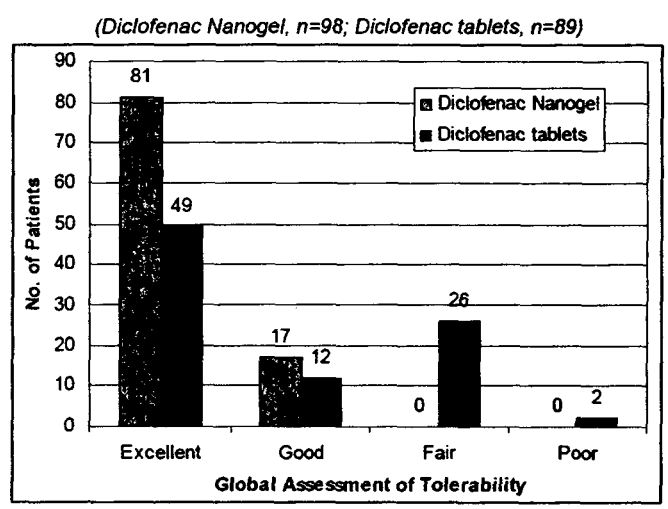
Figure 15: Overall assessment of tolerability at the end of study in patients with osteoarthritis (Clinical Study B).

METHOD FOR TREATMENT OF PAIN AND INFLAMMATION

RELATED APPLICATION INFORMATION

This application is a 371 of International Application PCT/IN2012/000016 filed 5 Jan. 2012 entitled "Method for Treatment of Pain and Inflammation", which was published in the English language on 31 Jan. 2013, with International Publication Number WO 2013/014680 A1 and which claims priority from Indian Patent Application 2156/MUM/2011, filed 28 Jul. 2011, the content of which is incorporated herein by reference.

FIELD OF THE INVENTION

The present invention relates to a method for the treatment of pain and inflammation. In particular, the present invention relates to a method for the treatment of musculoskeletal and connective tissue pain/inflammations. Further, the invention relates to reducing the incidence and severity of adverse events resulting from administration of diclofenac. The method comprises administration of a novel and stable pharmaceutical composition of diclofenac or its salt.

BACKGROUND OF THE INVENTION

Musculoskeletal and connective tissue inflammations are common diseases affecting a large human population. Some commonly seen musculoskeletal and connective tissue inflammations include osteoarthritis and associated articular and periarticular inflammations, and non-articular Rheumatism including capsulitis, tendonitis, fibrositis, and periarticular inflammations.

Osteoarthritis is the most common type of arthritis, especially among older people. Osteoarthritis is a joint disease that mostly affects the cartilage. Cartilage is the slippery tissue that covers the ends of bones in a joint. Healthy cartilage allows bones to glide over one another. It also absorbs energy from the shock of physical movement. In osteoarthritis, the surface layer of cartilage breaks down and wears away. This allows bones under the cartilage to rub together, causing pain, swelling, and loss of motion of the joint. Over time, the joint may lose its normal shape. Also, bone spurs may grow on the edges of the joint. Bits of bone or cartilage can break off and float inside the joint space. This causes more pain and damage. People with osteoarthritis usually have joint pain and limited movement. Unlike some other forms of arthritis, osteoarthritis only affects joints, and not internal organs.

Osteoarthritis is one of the most frequent causes of physical disability among adults. Some younger people get osteoarthritis from a joint injury, but osteoarthritis most often occurs in older people. In fact, by age 65, more than half of the population has x-ray evidence of osteoarthritis in at least one joint. Since the number of older people is increasing, so is the number of people with osteoarthritis. Both men and women have the disease.

Existing osteoarthritis treatment approaches include exercise, medicines, rest and joint care, surgery, pain relief techniques, alternative therapies, and weight control. The commonly used medicines in treating osteoarthritis include nonsteroidal anti-inflammatory drugs (NSAIDs), for example, diclofenac (Voveran® gel, tablet) aspirin, ibuprofen (Advil®, Motrin® IB), naproxen sodium (Aleve®), ketoprofen; topical pain-relieving creams, rubs, and sprays (for example, capsaicin cream) applied directly to the skin; corticosteroids, powerful anti-inflammatory hormones made naturally in the body or man made for use as drugs, typically injected into affected joints to relieve pain temporarily; and hyaluronic acid, a new medicine for joint injection, used to treat osteoarthritis of the knee. Surgery may be performed to resurface (smooth out) bones, reposition bones, and replace joints. For some people, surgery helps relieve the pain and disability of osteoarthritis. Osteoarthritis is a chronic disease. Although various medications have been used for treating the disease, they are not effective for long term control and prevention.

Many of the musculoskeletal and connective tissue inflammations are chronic and cause chronic regional pain and loss of functionality of affected areas.

Diclofenac is one of the routinely prescribed anti-inflammatory agents available for the management of musculoskeletal and connective tissue inflammations. It is marketed as injection, oral immediate release tablets, sustained release tablets and conventional topical formulations. The drug is almost completely absorbed after oral administration but is subjected to 50% hepatic first-pass metabolism.

Although a major portion of commercial diclofenac is available in the form of oral medications, the drug causes serious adverse effects in the gastrointestinal tract. Gastrointestinal (GI) bleeding and ulcerations are quite common due to oral diclofenac. Therefore, topical preparations like creams; ointments for external application are being widely used. However, since diclofenac and its salts are scarcely absorbed percutaneously and thereby require higher quantity to be applied topically thus leading to increased frequency of application also. This leads to patient incompliance.

U.S. Pat. No. 5,629,021 relates to micellar nanoparticles and methods of their production.

U.S. Patent Publication No. 2010/0029781 discloses a method of preparing a solvent-microparticle (SMP) topical gel formulation comprising a bioactive drug wherein the formulation comprises the drug dissolved in a liquid and the drug in a microparticulate solid form dispersed in the liquid.

U.S. Pat. No. 5,894,019 discloses topical compositions comprising lipid and essentially free of emulsifiers and surfactants.

European Patent No. EP 1536836 B1 discloses conventional topical emulsion gel of diclofenac sodium.

European Patent No. EP 506197 B1 discloses an aqueous suspension of solid lipid nanoparticles for topical use.

European Patent No. EP 0671903 B1 discloses topical compositions in the form of submicron oil spheres.

International (PCT) Publication No. 2008/051186 describes nanoemulsion compositions having anti-inflammatory activity.

Clinical evidence suggests that topically applied nonsteroidal antiinflammatory drugs (NSAIDs) are safer than and at least as efficacious as oral NSAIDs in the treatment of rheumatic diseases. Adverse drug reactions after topical administration of NSAID use are rare when compared to the incidence of serious GI events associated with oral NSAIDs. However, formulation may have a dramatic impact on depth of penetration at the site of application, retention of drug molecules within the layers of skin, concentrations achieved in the muscle tissue, synovial fluid and in systemic circulation.

Most of the topical preparations contain vehicles comprising permeation enhancers, solvents, and high amount of surfactants to achieve these goals. But use of these agents is harmful, especially in chronic application, as many of them are irritants. Therefore, a need to develop such topical preparations which does not involve use of such agents as described above to facilitate drug permeation through the skin, and still leads to excellent photostability, greater permeability, and improved bioavailability resulting in enhanced therapeutic pharmacodynamic activity is sought.

Thus, it is apparent that there still is a strong need for improved medications of diclofenac that can effectively treat musculoskeletal and connective issue pain or inflammations and related symptoms. A medication that can provide a long term control of musculoskeletal and connective tissue inflammations, inhibit further progress of existing conditions, and prevent reoccurrence of acute symptoms will have important medical significance for millions of people who suffer from these diseases.

SUMMARY OF THE INVENTION

In one general aspect there is provided a method for treating acute musculo-skeletal or connective tissue pain or inflammation, including osteoarthritis and associated articular and periarticular inflammations, and non-articular Rheumatism including capsulitis, tendonitis, fibrositis, and periarticular inflammations. The method comprises administering a topical pharmaceutical composition comprising nano size droplets of diclofenac or salts thereof.

In another general aspect there is provided a method for reducing pain intensity in patient suffering from acute musculoskeletal pain. The method comprises administering a topical pharmaceutical composition comprising nano size droplets of diclofenac or salts thereof.

In another general aspect there is provided a method for increasing pain relief in patient suffering from acute musculoskeletal pain. The method comprises administering a topical pharmaceutical composition comprising nano size droplets of diclofenac or salts thereof.

In another general aspect there is provided a method for reducing the incidence and severity of adverse events resulting from treatment of acute musculo-skeletal pain by the use of diclofenac or salt thereof, comprising administering a topical pharmaceutical composition comprising nano size droplets of diclofenac or salts thereof.

In another general aspect there is provided a method for decreasing usage of rescue medication in patient suffering from acute musculoskeletal pain comprising administering to said patient a topical pharmaceutical composition comprising nano size droplets of diclofenac or salts thereof.

In another general aspect there is provided a method for improving the local and systemic tolerability of diclofenac in patient suffering from acute musculoskeletal pain comprising administering to said patient a stable topical pharmaceutical composition comprising nano size droplets of diclofenac or salts thereof.

In another general aspect there is provided a method for reducing pain intensity in patient suffering from connective tissue inflammation. The method comprises administering a topical pharmaceutical composition comprising nano size droplets of diclofenac or salts thereof.

In another general aspect there is provided a method of improving WOMAC index pain sub-score in patient suffering from connective tissue inflammation. The method comprises administering a topical pharmaceutical composition comprising nano size droplets of diclofenac or salts thereof.

In another general aspect there is provided a method of improving WOMAC index total score in patient suffering from connective tissue inflammation. The method comprises administering a topical pharmaceutical composition comprising nano size droplets of diclofenac or salts thereof.

In another general aspect there is provided a method of improving WOMAC index stiffness sub-score in patient suffering from connective tissue inflammation. The method comprises administering a topical pharmaceutical composition comprising nano size droplets of diclofenac or salts thereof.

In another general aspect there is provided a method of improving WOMAC index physical function sub-score in patient suffering from connective tissue inflammation. The method comprises administering a topical pharmaceutical composition comprising nano size droplets of diclofenac or salts thereof.

In another general aspect there is provided a method for reducing the incidence and severity of adverse events resulting from treatment of connective tissue inflammation by the use of diclofenac, comprising administering a topical pharmaceutical composition comprising nano size droplets of diclofenac or salts thereof.

In another general aspect there is provided a method for decreasing usage of rescue medication in patient suffering from connective tissue inflammation comprising administering to said patient a topical pharmaceutical composition comprising nano size droplets of diclofenac or salts thereof.

In another general aspect there is provided a method for improving the local and systemic tolerability of diclofenac in patient suffering from connective tissue inflammation comprising administering to said patient a stable topical pharmaceutical composition comprising nano size droplets of diclofenac or salts thereof.

Embodiments of the method of treating musculoskeletal and connective tissue pain or inflammation may include one or more of the following features. Applying a topical pharmaceutical composition to the skin which composition further may includes one or more pharmaceutically acceptable excipients. For example, the pharmaceutically acceptable excipients may include one or more of lipids, oils, emulsifiers, initiators, pH adjusting agents, emollients, humectants, preservatives, chelating agents, thickening agent, and the like.

In one general aspect there is provided a method for treating musculoskeletal and connective tissue pain or inflammation comprising administering a topical pharmaceutical composition prepared by the process comprising:
a) combining an oily phase comprising diclofenac or salts thereof along with other pharmaceutically acceptable excipients with an aqueous phase to form an emulsion;
b) reducing the particle size of emulsion of step a) to a droplet size having $D_{90}$ particle size of less than 500 nm; and
c) mixing other pharmaceutically acceptable excipients to emulsion obtained in step b) and converting it into a suitable finished dosage form.

The details of one or more embodiments of the invention are set forth in the description below. Other features, objects and advantages of the invention will be apparent from the description and claims.

BRIEF DESCRIPTION OF DRAWINGS

FIG. 1: The change in pain intensity score in patients with acute musculoskeletal pain (Clinical Study A).

FIG. 2: The change in pain relief score in patients with acute musculoskeletal pain (Clinical Study A).

FIG. 3: Overall assessment of efficacy in patients with acute musculoskeletal pain at the end of study (Clinical Study A).

FIG. 4: Overall assessment of tolerability in patients with acute musculoskeletal pain at the end of study (Clinical Study A).

FIG. 5: The improvement in WOMAC index pain sub-score in patients with osteoarthritis (Clinical Study A).

FIG. 6: The improvement in WOMAC index total score in patients with osteoarthritis (Clinical Study A).

FIG. 7: The improvement in WOMAC index stiffness sub-score in patients with osteoarthritis (Clinical Study A).

FIG. 8: The improvement in WOMAC index physical function sub-score in patients with osteoarthritis (Clinical Study A).

FIG. 9: Overall assessment of efficacy at the end of study in patients with osteoarthritis (Clinical Study A).

FIG. 10: Overall assessment of tolerability at the end of study in patients with osteoarthritis (Clinical Study A).

FIG. 11: The improvement in WOMAC index pain sub-score in patients with osteoarthritis (Clinical Study B).

FIG. 12: The improvement in WOMAC index total score in patients with osteoarthritis (Clinical Study B).

FIG. 13: The improvement in WOMAC index stiffness sub-score in patients with osteoarthritis (Clinical Study B).

FIG. 14: The improvement in WOMAC index physical function sub-score in patients with osteoarthritis (Clinical Study B).

FIG. 15: Overall assessment of tolerability at the end of study in patients with osteoarthritis (Clinical Study B).

DETAILED DESCRIPTION OF THE INVENTION

The inventors of the invention have surprisingly found that when diclofenac or salts thereof is formulated into nano size droplets in pharmaceutically acceptable emulgel (emulsion gel) system which includes optimized ratios of oils and/or emulsifiers, the composition exhibits enhanced therapeutic efficacy and reduced incidence and severity of adverse events in patients suffering from musculoskeletal and connective tissue pain or inflammation (e.g. osteoarthritis).

In particular, the inventors have found that the composition of the present invention significantly reduces pain intensity and increases pain relief in. The composition was also found to reduce the incidence and severity of adverse events (such as local irritation, burning, redness, itching and rashes) resulting from administration of conventional topical compositions of diclofenac.

Further, advantageously the composition also posses stable thermodynamic properties and do not have the problems of creaming, flocculation, coalescence or sedimentation, which are commonly associated with macro-emulsion, thus ensuring better stability and longer shelf-life of the resulting product.

Moreover, the composition of the invention results in immediate and sustained action, covering large surface area with less quantity and posses good spreadability. The composition is also non-irritant to skin and mucous membranes, requires reduced frequency of application, thus leading to improved patient compliance and offers cosmetic benefits like non-stickiness, and non-greasy feel.

The terms "treating" or "treatment" of a state, disorder or condition as used herein means: (1) inhibiting the state, disorder or condition, i.e., arresting or reducing the development of the disease or at least one clinical or sub-clinical symptom thereof, or (2) relieving the disease, i.e., causing regression of the state, disorder or condition or at least one of its clinical or subclinical symptoms. The benefit to a subject to be treated is either statistically significant or at least perceptible to the patient or to the physician.

The term "rescue medication" as used herein is defined as an additional medication necessary to treat breakthrough or recurring symptoms.

The embodiments of the present invention relates to various methods related to treatment of musculoskeletal and connective tissue pain/inflammations. The method comprises of applying to the afflicted skin region a pharmaceutical composition comprising diclofenac or salts thereof in the form of nano size droplets, such as a non-gel emulsion.

In a preferred embodiment, the nano size droplets of diclofenac or salts thereof have a $D_{90}$ particle size of about 500 nm or less.

In a further embodiment, the nano size droplets of diclofenac or salts thereof have a $D_{90}$ particle size of about 250 nm or less, and more preferably about 100 nm or less.

In an embodiment, the method according to the present invention can be used to reduce the intensity of in patient suffering from acute musculoskeletal pain or connective tissue inflammation (e.g. osteoarthritis).

In a further embodiment, the method according to the present invention can be used to increase pain relief in patient suffering from acute musculoskeletal pain or connective tissue inflammation (e.g. osteoarthritis).

In a further embodiment, the method according to the present invention can be used to reduce the incidence and severity of adverse events resulting from treatment of acute musculo-skeletal pain or connective tissue inflammation (e.g. osteoarthritis).

In a further embodiment, the method according to the present invention can be used to decrease usage of rescue medication in patient suffering from acute musculoskeletal pain or connective tissue inflammation (e.g. osteoarthritis).

In a further embodiment, the method according to the present invention can be used to improve the local and systemic tolerability of diclofenac in patient suffering from acute musculoskeletal pain or connective tissue inflammation (e.g. osteoarthritis).

In a further embodiment, the composition comprises about 0.5% to about 5.0% w/w, and preferably about 0.5% to about 3.0% w/w of diclofenac or salt thereof (based on total weight of the composition).

The composition of the present invention may comprise one or more additional active agents suitable for treatment of musculo-skeletal or connective tissue inflammation or pain. Suitable active agents may be selected from one or more of non-steroidal anti-inflammatory and analgesic agents. In an embodiment, the composition comprises methyl salicylate.

The composition of the present invention further comprises one or more pharmaceutically acceptable excipients selected from, but not limited to lipids, oils, emulsifiers, initiators, pH adjusting agents, emollients, humectants, preservatives, and chelating agents.

The pH of the composition of the invention ranges from about 4.5 to about 7.0, and preferably from 5.0 to about 6.0.

Suitable lipids which can be used include one or more of hydrocarbons, fatty alcohols, fatty acids, glycerides or esters of fatty acids with $C_1$-$C_{36}$ alkanols. Hydrocarbons may include paraffin or petroleum jelly. Fatty alcohols may include decanol, dodecanol, tetradecanol, hexadecanol or octadecanol. Fatty acids may include $C_6$-$C_{24}$ alkanoic acids such as hexanoic acid, octanoic acid, decanoic acid, dodecanoic acid, tetradecanoic acid, hexadecanoic acid, octadecanoic acid, unsaturated fatty acids such as oleic acid and linoleic acid. Glycerides may include olive oil, castor oil, sesame oil, caprylic/capric acid triglyceride or glycerol mono-, di- and tri-esters with palmitic and/or stearic acid. Esters of fatty acids may include $C_1$-$C_{36}$ alkanols such as beeswax, carnauba wax, cetyl palmitate, lanolin, isopropyl myristate, isopropyl stearate, oleic acid decyl ester, ethyl oleate and $C_6$-$C_{12}$ alkanoic acid esters and the like.

Suitable oils which can be used include one or more of almond oil, apricot seed oil, borage oil, canola oil, coconut oil, corn oil, cotton seed oil, fish oil, jojoba bean oil, lard oil, linseed oil, boiled macadamia nut oil, mineral oil, olive oil, peanut oil, safflower oil, sesame oil, soybean oil, squalane, sunflower seed oil, tricaprylin (1,2,3 trioctanoyl glycerol), wheat germ oil and the like. The preferred quantity of oil used is in the range of about 5 to about 40% w/w, and more preferably in the range of about 5% to about 30% w/w of the composition.

Suitable emulsifiers which can be used include one or more of ionic polysorbate surfactant, Tween® 20, Tween® 40, Tween® 60, Tween® 80, Nonylphenol Polyethylene Glycol Ethers, (alkylphenol-hydroxypolyoxyethylene), Poly (oxy-1,2-ethanediyl), alpha-(4-nonylphenol)-omega-hydroxy-, branched (i.e. Tergitol® NP-40 Surfactant), Nonylphenol Polyethylene Glycol Ether mixtures (i.e. Tergitol® NP-70 (70% AQ) Surfactant), phenoxypolyethoxyethanols and polymers thereof such as Triton®, Poloxamer®, Spans®, Tyloxapol®, different grades of Brij, sodium dodecyl sulfate and the like. The preferred quantity of the emulsifiers used is in the range of about 0.1% to about 10% w/w of the composition.

In a preferred embodiment, the ratio of emulsifier to oil in the pharmaceutical composition of the present invention ranges from about 0.1:20 to about 0.1:1, preferably about 0.1:10 to about 0.1:1.

Suitable pH adjusting agents which can be used include one or more of organic or inorganic acids and bases including sodium hydroxide, potassium hydroxide, ammonium hydroxide, phosphate buffers, citric acid, acetic acid, fumaric acid, hydrochloric acid, malic acid, nitric acid, phosphoric acid, propionic acid, sulfuric acid, tartaric acid and the like.

Suitable emollients which can be used include one or more of caprylic/capric triglycerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, glyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, steareth-2 or -100, stearic acid, stearyl alcohol, urea and the like.

Suitable preservatives which can be used include one or more of phenoxyethanol, parabens (such as methylparaben and propylparaben), propylene glycols, sorbates, urea derivatives (such as diazolindinyl urea), and the like.

Suitable humectants which can be used include one or more of propylene glycol, glycerin, butylene glycol, sorbitol, triacetin and the like.

Suitable chelating agents which can be used include one or more of disodium EDTA, edetate trisodium, edetate tetrasodium, diethyleneamine pentaacetate and the like.

Suitable initiators may include one or more of alcohols like $C_1$-$C_{12}$ alcohols, diols and triols, glycerol, methanol, ethanol, propanol, octanol and the like.

In one embodiment, composition of the invention may be prepared by a) combining an oily phase comprising diclofenac or salts thereof along with other pharmaceutically acceptable excipients with an aqueous phase to form an emulsion; b) reducing the particle size of emulsion of step a) to a droplet size having $D_{90}$ particle size of less than about 500 nm; and c) mixing other pharmaceutically acceptable excipients to emulsion obtained in step b) and converting it into a suitable finished dosage form.

The nano size droplets may be produced with reciprocating syringe instrumentation, continuous flow instrumentation, high speed mixing or high pressure homogenization. However, it will appreciated to the person skilled in the art any known method of reducing the size of droplet may be adopted to serve the purpose of the present invention.

Small droplets of the nano emulsion may be formed by passing the emulsion through a homogenizer under different pressures ranging from 3,500-21,500 psi. The emulsion may be passed between 4-5 times under the same conditions to get a final $D_{90}$ droplet size of less than about 500 nm. The nano droplets formed may be filtered through 0.2 to 0.4 micron filter.

The gel base may be used in the present invention to form a gel matrix for the preparation of nanogel from nano emulsion. The gel base comprises of one or more of thickening agents.

Suitable thickening agents which can be used include one or more of cellulose polymer, a carbomer polymer, a carbomer derivative, a cellulose derivative, polyvinyl alcohol, poloxamers, polysaccharides and the like.

Suitable dosage form of the invention may include cream, gel, ointment, lotion, paste, liniment, and emulsion.

In a preferred embodiment, the composition of the invention is in the form of gel.

The present invention further provides use of a pharmaceutical composition comprising diclofenac or salts thereof in the form of nano size droplets, for reducing pain intensity; increasing pain relief; reducing the incidence and severity of adverse events resulting from topical application of diclofenac; decreasing usage of rescue medication; or improving the local and systemic tolerability of diclofenac in patient suffering from acute musculoskeletal pain or connective tissue inflammation.

The efficacy and safety of the composition of the present invention (Diclofenac Nanogel containing 1% diclofenac sodium) was evaluated vis-à-vis other Diclofenac Conventional gel formulation (Voveran® Gel [marketed by Novartis] containing 1% diclofenac sodium) and Diclofenac tablet formulation. It was observed that the formulation of the present invention was more effective in reducing pain intensity or increasing pain relief in patients with acute musculoskeletal pain and osteoarthritis and is better tolerated (both locally and systemically) than the conventional formulation. The composition of the present invention was also found to reduce the incidence and severity of adverse events resulting from its application when compared with the adverse events resulting from application of the marketed formulation.

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

Example 1: Diclofenac Sodium Nano Gel

TABLE 1

| Sr. No. | Ingredients | % w/w |
|---|---|---|
| | Nano emulsion | |
| 1 | Diclofenac sodium | 0.5-3 |
| 2 | Ethanol | 5-20 |
| 3 | Menthol | 0.01-1 |
| 4 | Polysorbate 80 (Tween 80) | 2-10 |
| 5 | Glycerol | 5-20 |
| 6 | Soyabean oil | 10-30 |
| 7 | Methyl salicylate | 0.5-5 |
| 8 | Water | 25-75 |
| | Nano gel | |
| 1 | Diclofenac sodium nanoemulsion | 25-50 |
| 2 | Carbopol gel (2% w/w) | 50-100 |

Procedure:

Diclofenac sodium and menthol were dissolved in ethanol and tween 80 mixture along with glycerol. This hydroalcoholic phase was mixed with soyabean oil and methyl salicylate. Water was added with stirring to the resulting mixture. The resulting blend was homogenized to reduce the droplet size to $D_{90}$ particle size of about 250 nm with the help of high pressure homogenization to get the nano emulsion. Carbomer was added to water for hydration and kept overnight to ensure complete hydration. The aqueous dispersion of carbomer was mixed with nano emulsion to get nanogel.

Example 2: Clinical Study A

The efficacy and safety of the composition of the present invention (Diclofenac Nanogel) was evaluated vis-à-vis Diclofenac conventional gel (Voveran® Gel [marketed by Novartis, containing 1% diclofenac sodium].

A randomized, open label, comparative, multicentric study to assess the efficacy and safety of composition of the present invention (Diclofenac Nanogel) in comparison with Diclofenac conventional gel in acute musculo-skeletal pain or osteoarthritis was carried out by pain intensity on visual analogue scale (VAS from 0 to 100 mm) and pain relief score evaluated at baseline and at Days 3, 7, 10 & 14 or till complete pain relief, whichever was earlier. In osteoarthritis, efficacy assessments were carried out by WOMAC (Western Ontario and McMaster Universities Osteoarthritis) index score evaluated at baseline and at Week 1, 2, 3 & 4. Clinical safety assessments were carried out on the scheduled outpatient visits.

A total of 359 patients in were enrolled in the study, which included 122 patients suffering from acute musculoskeletal pain and 237 patients suffering from osteoarthritis in this randomized, open label, comparative, multicentric, clinical trial to assess the efficacy and safety of Diclofenac Nanogel 2-4 gm applied four times daily in comparison with Diclofenac conventional gel (Voveran® gel) 2-4 gm applied four times daily.

Among patients suffering from acute musculoskeletal pain; 62 patients were allocated to Diclofenac Nanogel group and 60 patients were allocated to Diclofenac conventional gel group. Further, among osteoarthritis patients, 133 patients received Diclofenac Nanogel and 104 patients received Diclofenac conventional gel according to a centralized computer generated randomization schedule.

Patients were instructed to apply 2-4 gm of either Diclofenac Nanogel or Diclofenac conventional gel (Voveran® gel), depending upon the size of the area to be treated, and gently rub on the affected area 4 times daily. The total treatment duration in patients suffering from acute painful musculoskeletal disorders was a maximum of 14 days or till complete pain relief is obtained, whichever was earlier. While, the total treatment duration in patients suffering from osteoarthritis was 4 weeks.

In the treatment of patients with acute musculoskeletal pain, Diclofenac Nanogel 2-4 gm applied four times daily was found to have a significantly better therapeutic efficacy as compared to Diclofenac conventional gel applied similarly in the primary efficacy variables i.e., the degree of improvement in pain intensity on visual analogue scale (FIG. 1) and secondary efficacy variables of the degree of improvement in pain score (FIG. 2) and investigators' global assessment of efficacy (FIG. 3). Diclofenac Nanogel was found to be significantly more effective than Diclofenac conventional gel in providing pain relief as early as after 7 days of therapy.

Further, in the treatment of patients with osteoarthritis, Diclofenac Nanogel was similarly found to have a significantly better therapeutic efficacy as compared to Diclofenac conventional gel in the primary efficacy variable of improvement in the pain sub-score of WOMAC Index (Table 3, FIG. 5) as well as secondary efficacy variables of other aspects of WOMAC index i.e. stiffness (Table 3, FIG. 7), physical function (Table 3, FIG. 8) & total score (Table 3, FIG. 6) and investigators' global assessment of efficacy (FIG. 9). In this study indication also, Diclofenac Nanogel was reported to be significantly more effective than Diclofenac conventional gel as early as after 1 week of therapy. The reduction in requirement of rescue medication during the course of study was significantly more with Diclofenac Nanogel as compared to Diclofenac conventional gel.

At the end of study, as per the investigators' overall assessment of efficacy in Diclofenac Nanogel group a larger number of patients in each of the indication were rated to have an "excellent" efficacy to the study medication at the end of the study (50 (80.6%) & 76 (57.1%) vs. 5 (8.3%) & 7 (6.7%), in acute musculoskeletal pain and osteoarthritis respectively, (FIGS. 3 & 9).

Thus, in patients suffering from acute musculoskeletal pain or osteoarthritis, Diclofenac Nanogel was significantly more effective in all the efficacy parameters than Diclofenac conventional gel (Tables 2 & 4).

TABLE 2

Summary of efficacy findings in acute musculoskeletal pain
(Mean ± S.D. [95% CI]/No. (%))

| Sr. No. | Efficacy variables | Mean Change | | | % complete improvement | | |
|---|---|---|---|---|---|---|---|
| | | Diclofenac Nanogel | Diclofenac conventional gel | P Value | Diclofenac Nanogel | Diclofenac conventional gel | P Value |
| 1. | Pain on VAS | 72.7 ± 11.6 [69.8-75.6] | 44.5 ± 16.1 [40.4-48.6] | <0.001 | 52 (83.9%) | 5 (8.3%) | <0.001 |
| 2. | Pain Relief Score | 3.8 ± 0.7 [3.6-4.0] | 2.7 ± 0.8 [2.5-2.9] | <0.001 | — | — | — |

TABLE 3

Summary of efficacy findings in both the study groups
(Mean ± S.D. [95% CI]/No. (%))

| Sr. No. | Efficacy variables | Mean Change | | | % complete improvement | | |
|---|---|---|---|---|---|---|---|
| | | Diclofenac Nanogel | Diclofenac conventional gel | P Value | Diclofenac Nanogel | Diclofenac conventional gel | P Value |
| 1. | WOMAC-Pain | 11.9 ± 4.4 [11.1-12.6] | 8.8 ± 3.9 [8.0-9.5] | <0.001 | 35 (26.3%) | 5 (4.8%) | <0.001 |
| 2. | WOMAC-Stiffness | 5.2 ± 2.0 [4.9-5.6] | 3.9 ± 1.6 [3.6-4.3] | <0.001 | 51 (38.3%) | 8 (7.7%) | <0.001 |
| 3. | WOMAC-Physical function | 37.6 ± 16.4 [34.8-40.4] | 20.7 ± 12.6 [18.4-23.1] | <0.001 | 29 (21.8%) | 3 (2.9%) | <0.001 |
| 4. | WOMAC index-Total | 54.7 ± 16.4 [51.0-58.4] | 31.3 ± 15.5 [28.3-34.3] | <0.001 | 24 (18.0%) | 2 (1.9%) | <0.001 |

On the tolerability front, Diclofenac Nanogel were found to be equally well tolerated or slightly better as compared to Diclofenac conventional gel with a similar profile of adverse events being reported in each group during the course of the study (Tables 4, 5, 6 & 7).

TABLE 4

List of Adverse Events with Diclofenac Nanogel (n = 62)

| Sr. No. | Nature of Adverse Event | Number | % incidence |
|---|---|---|---|
| 1. | Irritation | 2 | 3.2 |
| 2. | Redness | 2 | 3.2 |
| 3. | Rash | 1 | 1.6 |
| | Total | | 5 events |

TABLE 5

List of Adverse Events with Diclofenac conventional gel (n = 60)

| Sr. No. | Nature of Adverse Event | Number | % incidence |
|---|---|---|---|
| 1. | Irritation | 4 | 6.7 |
| 2. | Redness | 3 | 5.0 |
| 3. | Rash | 1 | 1.7 |
| | Total | | 8 events |

TABLE 6

List of Adverse Events with Diclofenac Nanogel (n = 133)

| Sr. No. | Nature of Adverse Event | Number | % incidence |
|---|---|---|---|
| 1. | Irritation | 3 | 2.3 |
| 2. | Itching | 1 | 0.8 |
| | Total | | 4 events |

TABLE 7

List of Adverse Events with Diclofenac conventional gel (n = 104)

| Sr. No. | Nature of Adverse Event | Number | % incidence |
|---|---|---|---|
| 1. | Irritation | 3 | 14.4 |
| 2. | Itching | 2 | 1.9 |
| 3. | Redness | 5 | 4.8 |
| 4. | Rash | 2 | 1.9 |
| | Total | | 24 events |

Further, the usage of rescue medication (number of Paracetamol 500 mg tablets consumed per week) decreased significantly in Diclofenac Nanogel group as well as Diclofenac conventional gel group, which was however comparable in each group (Table 8).

TABLE 8

Change in the rescue medication usage
during the study in Osteoarthritis

| Study Group | Study Duration | | Change in Usage | |
| --- | --- | --- | --- | --- |
| | Week 1 | Week 4 | [95% CI] | P value |
| Diclofenac Nanogel (n = 133) | 3.6 ± 3.8 | 0.8 ± 1.2 | 2.8 ± 3.9 [2.2-3.5] | 0.022 |
| Diclofenac conventional gel (n = 104) | 4.2 ± 4.3 | 2.5 ± 3.4 | 1.7 ± 3.7 [1.0-2.4] | |

Although, the adverse events' incidence was not significantly different between Diclofenac Nanogel and Diclofenac conventional gel in acute musculoskeletal pain indication, it reached statistical significance; particularly for local irritation, in the indication of OA which studied the medications for a longer duration. This difference can be explained by the duration of exposure which was substantially longer during the usage in OA. The adverse events reported in Diclofenac Nanogel group were also of less severe intensity than those reported in Diclofenac conventional gel group. The common adverse events with relevant causal association reported in both the groups were local application site reactions particularly irritation and burning sensation. All the adverse events resolved completely with or without symptomatic treatment during the course of study.

In addition, 97.0% & 91.9% in Diclofenac Nanogel group and 90.0% & 79.8% in Diclofenac conventional gel group were rated to have an "excellent" tolerability to the study medication as per the 4-point global assessment of tolerability for the indication of acute musculoskeletal pain & osteoarthritis, respectively (FIGS. 4 & 10). It was noticeable that with incidence of adverse event was more with prolonged usage in osteoarthritis as compared to acute pain in each treatment group; however the increase in incidence was more pronounced in Diclofenac conventional gel group as compared to Diclofenac Nanogel group.

The result of the above clinical study demonstrated that Diclofenac Nanogel 2-4 gm applied four times daily is significantly more effective as compared to Diclofenac conventional gel (Voveran® gel) 2-4 gm applied four times daily in patients suffering from acute musculo-skeletal pain or osteoarthritis; while on the tolerability front Diclofenac Nanogel is as well tolerated or slightly better tolerated than Diclofenac conventional gel.

Example 3: Clinical Study B

The efficacy and safety of the composition of the present invention (Diclofenac Nanogel) was evaluated vis-à-vis Diclofenac 50 mg Tablets (Voveran® Tablets [marketed by Novartis].

A randomized, open label, comparative, multicentric study to assess the efficacy and safety of Diclofenac Nanogel in comparison with Diclofenac tablets was performed in patients suffering from osteoarthritis. Efficacy assessments were carried out by WOMAC (Western Ontario and McMaster Universities Osteoarthritis) index score evaluated at baseline and at Week 1, 2, 3 & 4. Clinical safety assessments were carried out on the scheduled out-patient visits.

Patients were instructed to apply 2-4 gm of either Diclofenac Nanogel, depending upon the size of the area to be treated, and gently rub on the affected area four times daily or to take Diclofenac 50 mg tablets (Voveran® tablets) three times daily for the entire duration of study i.e. 4 weeks.

In the treatment of patients with osteoarthritis, Diclofenac Nanogel 2-4 gm applied four times daily had a comparable efficacy to Diclofenac 50 mg tablets (Voveran® tablets) given thrice daily in the primary efficacy variable i.e., the degree of improvement in the pain sub-score of WOMAC Index at the end of therapy and at each follow-up visit as compared to baseline (FIG. 11). Number of patients attaining complete pain relief was also not significantly different across the study groups.

Further, in the secondary efficacy parameter of improvement in WOMAC index stiffness sub-score both the study medication were found to be equally effective (FIG. 13). In the WOMAC index sub-score for physical function, while the reduction in mean total score was significantly more with Diclofenac Nanogel (FIG. 14); number of patients attaining complete improvement (with a mean score of zero) was significantly higher with Diclofenac tablets. Similarly for WOMAC index total score also, the reduction in mean total score was significantly better with Diclofenac Nanogel (FIG. 12); while number of patients attaining a mean total score of zero at the end of study was significantly higher with Diclofenac tablets. The reduction in requirement of rescue medication was comparable in both the study groups (Table 9).

TABLE 9

Change in the rescue medication usage during the study

| Study Group | Study Duration | | Change in Usage | |
| --- | --- | --- | --- | --- |
| | Week 1 | Week 4 | [95% CI] | P value |
| Diclofenac Nanogel (n = 98) | 3.6 ± 3.1 | 0.7 ± 1.3 | 2.9 ± 2.7 [2.4-3.4] | 0.739 |
| Diclofenac tablets (n = 89) | 5.1 ± 5.3 | 2.4 ± 4.3 | 2.7 ± 3.3 [2.1-3.4] | |

Thus, while the degree of change in pain, stiffness, physical function and total WOMAC scores was generally more in Diclofenac Nanogel group (although statistically significant only for physical function and total score); the number of patients attaining complete improvement for all the parameters (except stiffness) were more in Diclofenac conventional gel group (also statistically significant for physical function and total score). These findings suggest that, while Diclofenac Nanogel produces a consistent response among all patients; the degree of symptomatic improvement may be larger with Diclofenac tablets in patients who respond to the oral formulation.

Thus, in patients suffering from osteoarthritis, Diclofenac Nanogel have comparable efficacy to Diclofenac tablets (Voveran® tablets), (Table 10).

TABLE 10

Summary of efficacy findings in both the study groups
(Mean ± S.D. [95% CI]/No. (%))

| Sr. No. | Efficacy variables | Mean Change | | | % complete improvement | | |
|---|---|---|---|---|---|---|---|
| | | Diclofenac Nanogel | Diclofenac tablets | P Value | Diclofenac Nanogel | Diclofenac tablets | P Value |
| 1. | WOMAC-Pain | 11.9 ± 3.7 [10.9-12.3] | 10.5 ± 4.4 [9.5-11.4] | 0.06 | 9 (9.2%) | 13 (14.6%) | 0.25 |
| 2. | WOMAC-Stiffness | 5.1 ± 1.5 [4.8-5.4] | 4.6 ± 1.8 [4.2-5.0] | 0.052* | 29 (29.6%) | 16 (18.0%) | 0.063 |
| 3. | WOMAC-Physical function | 39.3 ± 11.6 [37.0-5.4] | 35.3 ± 13.4 [32.5-38.1] | 0.033* | 1 (1.0%) | 9 (10.1%) | 0.006* |
| 4. | WOMAC index-Total | 56.3 ± 15.9 [52.8-59.2] | 50.5 ± 18.9 [46.5-54.4] | 0.026* | 1 (1.0%) | 8 (9.0%) | 0.014* |

*Statistically significant P values

On the tolerability front, Diclofenac Nanogel was found to be significantly better tolerated as compared to Diclofenac tablets (Tables 11 & 12). A significantly lesser incidence of adverse events was reported with Diclofenac Nanogel as compared to Diclofenac tablets. While the adverse events reported with Diclofenac Nanogel were of only "mild" intensity; the adverse events in Diclofenac tablets groups also included many "moderate" to "severe" intensity events. Adverse event profiles reported with Diclofenac Nanogel and Diclofenac tablets were different. The commonest adverse events with Diclofenac Nanogel were local in nature; while those with Diclofenac tablets were gastrointestinal in nature. Further, no drug discontinuation related to adverse event was reported in Diclofenac Nanogel group; while 2 drug discontinuations due to gastrointestinal adverse events were reported in Diclofenac tablets group. All these adverse events settled completely with/without symptomatic treatment.

TABLE 11

List of Adverse Events with Diclofenac Nanogel (n = 98)

| Sr. No. | Nature of Adverse Event | Number | % incidence |
|---|---|---|---|
| 1. | Local Irritation/Burning sensation | 11 | 11.2 |
| 2. | Dryness | 3 | 3.1 |
| 3. | Skin rash | 2 | 2.0 |
| 4. | Erythema | 1 | 1.0 |
| | Total | 17 events | |

TABLE 12

List of Adverse Events with Diclofenac tablets (n = 89)

| Sr. No. | Nature of Adverse Event | Number | % incidence |
|---|---|---|---|
| 1. | Acidity/Gastritis | 22 | 24.7 |
| 2. | Abdominal pain | 6 | 6.7 |
| 3. | Vomiting | 6 | 6.7 |
| 4. | Nausea | 5 | 5.6 |
| 5. | Diarrhea | 4 | 4.5 |
| 6. | Anorexia | 2 | 2.2 |
| 7. | Hypertension | 2 | 2.2 |
| 8. | Allergic reaction | 1 | 1.1 |
| | Total | 48 events | |

In addition, 82.7% patients enrolled in Diclofenac Nanogel group were rated to have an "excellent" tolerability to the study medication at the end of the study; while it was so in only 55.1% patients in Diclofenac tablets group (FIG. 15).

The result of the above clinical study demonstrated that efficacy of Diclofenac Nanogel is comparable to Diclofenac tablets in patients suffering from Osteoarthritis; while on the tolerability front Diclofenac Nanogel is significantly better tolerated than Diclofenac tablets.

While the invention has been described in terms of its specific embodiments, certain modifications and equivalents will be apparent to those skilled in the art and are intended to be included within the scope of the invention.

We claim:

1. A method for treating acute musculoskeletal or connective tissue pain or inflammation comprising one or more of osteoarthritis, articular inflammation, periarticular inflammation, non-articular rheumatism, capsulitis, tendonitis, fibrositis, and periarticular inflammation condition, the method comprising administering a topical pharmaceutical nanogel composition of diclofenac or a salt thereof, the nanogel composition consisting of a nanoemulsion and a gel base, wherein the nanoemulsion consists of nano size droplets of diclofenac or a salt thereof having a particle size ($D_{90}$) of about 100 nm or less, 5% to 30% w/w oils/lipids, 0.1% to 10% w/w of emulsifiers selected from the group consisting of ionic polysorbate surfactant, nonylphenol polyethylene glycol ethers, (alkylphenol-hydroxypolyoxyethylene), poly(oxy-1,2-ethanediyl), alpha-(4-nonylphenol)-omega-hydroxy-, branched, nonylphenol polyethylene glycol ether mixtures, phenoxypolyethoxyethanols and polymers thereof, brij, and sodium dodecyl sulfate, and one or more pharmaceutically acceptable excipients consisting of initiators, pH adjusting agents, thickening agents, emollients, humectants, preservatives, and chelating agents.

2. The method as claimed in claim 1, wherein the emulsifiers and oil are present in the composition in a weight ratio of from about 0.1:20 to about 0.1:1.

3. The method as claimed in claim 1, wherein the composition comprises diclofenac or a salt thereof, and one or more pharmaceutically acceptable excipients, wherein the composition is prepared by a process comprising:
   a) combining an oily phase comprising diclofenac or a salt thereof along with other pharmaceutically acceptable excipients with an aqueous phase to form an emulsion;
   b) reducing the particle size of emulsion of step a) to a droplet size having a particle size ($D_{90}$) of about 100 nm or less; and c) mixing the other pharmaceutically acceptable excipients to the emulsion obtained in step b) and converting it into a suitable finished dosage form.

4. A method for reducing pain intensity and/or increasing pain relief in patient suffering from acute musculoskeletal pain and/or connective tissue inflammation as claimed in claim 1, the method comprising administering a topical pharmaceutical nanogel composition of diclofenac or a salt thereof, the nanogel composition consisting of a nanoemulsion and a gel base, wherein the nanoemulsion consists of nano size droplets of diclofenac or a salt thereof having a particle size ($D_{90}$) of about 100 nm or less, 5% to 30% w/w oils/lipids, 0.1% to 10% w/w of emulsifiers selected from the group consisting of ionic polysorbate surfactant, nonylphenol polyethylene glycol ethers, (alkylphenol-hydroxypolyoxyethylene), poly(oxy-1,2-ethanediyl), alpha-(4-nonylphenol)-omega-hydroxy-, branched, nonylphenol polyethylene glycol ether mixtures, phenoxypolyethoxyethanols and polymers thereof, brij, and sodium dodecyl sulfate, and one or more pharmaceutically acceptable excipients consisting of initiators, pH adjusting agents, thickening agents, emollients, humectants, preservatives, and chelating agents.

5. A method for reducing the incidence and severity of adverse events resulting from treatment of acute musculoskeletal pain and/or connective tissue inflammation as claimed in claim 1, the method comprising administering a topical pharmaceutical nanogel composition of diclofenac or a salt thereof, the nanogel composition consisting of a nanoemulsion and a gel base, wherein the nanoemulsion consists of nano size droplets of diclofenac or a salt thereof having a particle size ($D_{90}$) of about 100 nm or less, 5% to 30% w/w oils/lipids, 0.1% to 10% w/w of emulsifiers selected from the group consisting of ionic polysorbate surfactant, nonylphenol polyethylene glycol ethers, (alkylphenol-hydroxypolyoxyethylene), poly(oxy-1,2-ethanediyl), alpha-(4-nonylphenol)-omega-hydroxy-, branched, nonylphenol polyethylene glycol ether mixtures, phenoxypolyethoxyethanols and polymers thereof, brij, and sodium dodecyl sulfate, and one or more pharmaceutically acceptable excipients consisting of initiators, pH adjusting agents, thickening agents, emollients, humectants, preservatives, and chelating agents.

6. The method as claimed in claim 1, where in the method comprises decreasing the usage of rescue medication.

7. A method for improving the local and systemic tolerability of diclofenac in a patient suffering from acute musculoskeletal pain and/or connective tissue inflammation as claimed in claim 1, the method comprising administering a topical pharmaceutical nanogel composition of diclofenac or a salt thereof, the nanogel composition consisting of a nanoemulsion and a gel base, wherein the nanoemulsion consists of nano size droplets of diclofenac of a salt thereof having a particle size ($D_{90}$) of about 100 nm or less, 5% to 30% w/w oils/lipids, 0.1% to 10% w/w of emulsifiers selected from the group consisting of ionic polysorbate surfactant, nonylphenol polyethylene glycol ethers, (alkylphenol-hydroxypolyoxyethylene), poly(oxy-1,2-ethanediyl), alpha-(4-nonylphenol)-omega-hydroxy-, branched, nonylphenol polyethylene glycol ether mixtures, phenoxypolyethoxyethanols and polymers thereof, brij, and sodium dodecyl sulfate, and one or more pharmaceutically acceptable excipients consisting of initiators, pH adjusting agents, thickening agents, emollients, humectants, preservatives, and chelating agents.

8. A method of improving Western Ontario and McMaster Universities Osteoarthritis (WOMAC) index total score in a patient suffering from connective tissue inflammation as claimed in claim 1, the method comprising administering a topical pharmaceutical nanogel composition of diclofenac or a salt thereof, the nanogel composition consisting of a nanoemulsion and a gel base, wherein the nanoemulsion consist of nano size droplets of diclofenac or a salt thereof having a particle size ($D_{90}$) of about 100 nm or less, 5% to 30% w/w oils/lipids, 0.1% to 10% w/w of emulsifiers selected from the group consisting of ionic polysorbate surfactant, nonylphenol polyethylene glycol ethers, (alkylphenol-hydroxypolyoxyethylene), poly(oxy-1,2-ethanediyl), alpha-(4-nonylphenol)-omega-hydroxy-, branched, nonylphenol polyethlene glycol ether mixtures, phenoxypolyethoxyethanols and polymers thereof, brij, and sodium dodecyl sulfate, and one or more pharmaceutically acceptable excipients consisting of initiators, pH adjusting agents, thickening agents, emollients, humectants, preservatives, and chelating agents.

9. The method as claimed in claim 8, wherein the Western Ontario and McMaster Universities Osteoarthritis (WOMAC) index total score comprises pain sub-score, stiffness sub-score, and/or physical function sub-score.

\* \* \* \* \*